United States Patent [19]

Lee et al.

[11] Patent Number: 4,859,528

[45] Date of Patent: * Aug. 22, 1989

[54] COMPOSITE TOOLING

[75] Inventors: Frank W. Lee, San Ramon; Jon D. Neuner, Pittsburg; Kenneth Baron, San Ramon, all of Calif.

[73] Assignee: Hexcel Corporation, Dublin, Calif.

[*] Notice: The portion of the term of this patent subsequent to May 3, 2005 has been disclaimed.

[21] Appl. No.: 128,382

[22] Filed: Dec. 3, 1987

Related U.S. Application Data

[63] Continuation-in-part of Ser. No. 39,175, Apr. 17, 1987, Pat. No. 4,742,148.

[51] Int. Cl.⁴ .................... C08G 59/68; C08L 63/00
[52] U.S. Cl. .................................. 428/290; 428/272; 428/273; 523/445; 523/466; 523/468; 528/94
[58] Field of Search ............... 523/445, 466, 468; 428/273, 272, 290; 528/94

[56] References Cited

U.S. PATENT DOCUMENTS

| | | | |
|---|---|---|---|
| 3,962,184 | 6/1976 | Notomi et al. | 528/220 X |
| 4,335,228 | 6/1982 | Beitchman et al. | 528/117 X |
| 4,558,115 | 12/1985 | Hefner | 528/117 X |
| 4,559,398 | 12/1985 | Tesch et al. | 528/117 X |
| 4,587,311 | 5/1986 | Schmid et al. | 528/117 X |
| 4,742,148 | 5/1988 | Lee et al. | 528/117 |

*Primary Examiner*—Earl Nielsen
*Attorney, Agent, or Firm*—Oblon, Spivak, McClelland, Maier & Neustadt

[57] ABSTRACT

A composite tooling part having excellent dimensional stability, which may be prepared at low cost employs a one-component epoxy resin system having a catalyst which is the reaction product of an aromatic dicyanate and an imidazole. Reinforcing materials are incorporated in the matrix, and the resulting prepreg is allowed to cure at low temperature, down to about room temperature, until the free standing state is obtained. Thereafter, if elevated temperature performance is necessary, the product can be post-cured at elevated temperatures, without the need for a high temperature master.

15 Claims, No Drawings

COMPOSITE TOOLING

This is a continuation-in-part of application Ser. No. 07/039,175 filed Apr. 17, 1987, and issued as U.S. Pat. No. 4,742,148 on May 3, 1988.

BACKGROUND OF THE INVENTION

1. Field of the Invention:

This invention pertains to the preparation of tooling for the manufacture of composite parts, and specifically comprises a tooling prepreg which prepreg has a freezer shelf-life of over 6 months and which cures to free standing stability at room temperature, and can be subsequently cured to withstand temperatures as high as 350° F.

BACKGROUND OF THE INVENTION

As the cost of energy continues to escalate, and performance demands placed on the transportation industry, and the aerospace industry, in particular, continue to increase, a search goes on for alternative methods of preparing new parts and products which can meet the elevated performance standards, withstand high temperature, and are yet lightweight and otherwise energy conservative. One of the most promising avenues of development lies in the production of composite parts, that is, parts made of a resin matrix, wherein the matrix is reinforced with a non-resin reinforcing body, generally and preferably, reinforcing fibers of a high modulus, such as fiberglass, graphite or boron. In the preferred high performance examples, these reinforcing fibers are highly oriented, according to a specific plan, to give enhanced performance under load.

Quite frequently, the resin matrix is, e.g., an epoxy resin, which requires elevated temperatures, up to and including above 350° F., for curing.

One critical element in this composite part production system is the mold. Generally, a preform, comprised of wet, uncured, or B-staged resin, coated on and surrounding the reinforcing fibers, is placed inside a mold, which is essential in retaining the shape of the desired article. In the absence of the mold, the preform will fall apart. In any event, the presence of the mold is frequently necessary to apply the pressure required for ultimate curing.

To insure both accuracy and precision, it is necessary to have a mold, or tooling part, which either has an extremely low coefficient of expansion, or has a coefficient of expansion very similar to the composite part to be prepared. Materials exhibiting low or no coefficient of thermal expansion are very rare and expensive, and difficult to machine. Composite materials, generally prepared from the same resins and reinforcing materials the ultimate composite part is to be prepared from would, however, have thermal expansion properties extremely close to those desired. Accordingly, composite tooling is a logical choice for the preparation of composite parts.

To date, the preparation of composite tooling has not been entirely successful.

Most composite resins that would withstand the curing temperatures and pressures generally required themselves must be cured at extremely high temperatures. This presents two problems. First, when a composite tooling article is initially gelled at high temperature, the large differences between the coefficient of thermal expansion in the resin and the reinforcing fibers cause huge residual stresses to build up at the fiber/resin interface, when the tooling cools down. These residual stresses can cause a drop both in part stability and mechanical properties. It is also difficult to produce a master (mold for the tool) which can withstand the higher temperatures of resin curing and exhibit no distortion when cycled hot and cold, and which will expand and contract at the same rate as the material being used to make the tool.

Accordingly, recent efforts have been directed at providing a tooling material which can be cured, or at least preliminarily cured, at low or room temperatures, which would eliminate the need for very expensive high temperature stable mastering materials, and make the production of high temperature tooling less costly and complicated. These attempts have similarly been largely unsuccessful.

Most of the systems are "two-component" wet lay-up formulations, that is, the complete resin monomer system and the catalyst are separated, until actual preparation is underway. These two-component systems are extremely difficult to use. Even when prepared, the resulting wet lay-up is initially set up at room temperature, in several days, and post cured, free standing, in an oven under a very complicated cure cycle. A typical cure profile calls for heating for two hours or more at 40° C., followed by one to two hours at 80° C., one hour at 120° C., one hour at 150° C., one hour at 180° C., one hour at 200° C., etc. The heating rate must be carefully controlled, having a maximum of 1° C./min. This very slow step-by-step cure profile must be used, otherwise mechanical properties, and most importantly, the dimensional accuracy of the tooling, will suffer. This puts enormous pressure on production schedules, and makes the composite tool obtained prohibitively expensive.

This two-component wet lay-up method also causes other problems in manufacture, such as the exposure of workers to hazardous materials such as amines or other irritative components, inconsistent, poor quality laminates due to the nature of the two-component system, an operation which cannot be clean, and is both time and space consuming, which is directly at odds with the short work-life, usually not more than a few hours, of the formulation after mixing of the two components. Thus, a time comsuming operation must be performed hastily, before the resin "sets". These inconsistent limitations give rise to expensive, and frequently imperfect, results. To further complicate matters, if an extremely large tool is to be prepared, or several tools are to be prepared at once, to lower cost, the reaction being exothermic, potential for extremely high heat release, or explosion, is present.

Thus, the need continues for a composite tool which can be prepared without complicated cure profiles, does not need to be initially cured at extremely high temperatures, and otherwise avoids the problems of a two-component system.

SUMMARY OF THE INVENTION

This invention employs the one-component latent epoxy resin catalyst system initially disclosed in commonly assigned patent application 07/039,175, filed Apr. 17, 1987, now U.S. Pat. No. 4,742,148, issued May 3, 1988. The latent epoxy resin system comprises a catalyst which is an imidazolcyanate adduct, having the formula:

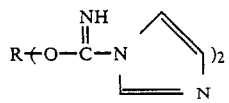

which is admixed with an epoxy resin prepolymer. R is generally an aromatic or aralkyl group, which may contain hetero atoms. The carbon moieties of the imidazole ring may be individually substituted or unsubstituted. Substituent groups for each position included $C_{1-12}$ alkyl, aryl and arakyl. Ideal resins are prepared from those based on polyglycidyl ether, and contain the catalyst in amounts of 0.1–20%, by weight. The entire disclosure of U.S. Pat. No. 4,742,148 is incorporated herein by reference. The catalyst disclosed therein, and the resin system including it, is an improvement on that disclosed in U.S. Pat. No. 4,533,715, also commonly assigned.

The inventive resin is transformed into a composite tooling part first by forming a prepreg through the incorporation of the reinforcing fibers, according to well established prior art methods, which can involve any of a variety of wet forming prior art methods such as vacuum bagging or press molding. (The preparation of composite parts, made using the tooling of this invention themselves, per se, does not constitute an aspect of this invention, and is not disclosed in detail, herein). The prepared tool is initially cured, to free standing condition, in 7–10 days under room temperature. Of course, initial curing may be accelerated by exposure to higher temperatures, e.g., up to about 250° F. However, lower temperatures, within about 30° F. of room temperature, are preferred. If elevated temperature properties are required, i.e., if the tool is to be used to prepare parts that must be cured at elevated temperatures up to about 370° F., the tool can be subsequently post-cured, free standing, up to these temperatures or slightly higher to increase surface temperature, with no complicated heating cycle.

As this is a one-component prepreg system, the handling of the system and the requisite materials is safe, and can be maintained clean. Since it is a prepreg system, precise fiber volume and resin amounts can be predetermined to obtain optimum performance for the tool. Very consistent and high quality materials can be prepared. Since gelation occurs at room temperature, this system produces composite tools with very low residual stress levels and minimization of the microcracking which deliteriously effects the tool life and properties of conventional hot cured prepreg tooling. Additionally, the low initial curing temperature allows previous curing distortion phenomena encountered in high temperature tooling to be eliminated, thus, providing a heretofore unattainable level of dimensional accuracy, particularly in light of the absence of any inaccuracies arising from thermal expansion of the master.

DETAILED DESCRIPTION OF THE INVENTION

The epoxy resin system, which constitutes the heart of this invention, is fully disclosed in the afore reference U.S. patent application 07/039,175. Therein, considerations are discussed concerning the relative balance between the catalyst and the epoxy resin, particularly, solubility of the catalyst in the resin system, and the availability of crosslinking sites to the catalyst. For the inventive system to perform well, the balance of the solubility of the selected catalyst and the resin mixture, the amount of crosslinking sites available from the epoxy resin and the final "tack and drape" of the prepreg are very important. One way to induce a much higher Tg than Tcure in a tooling resin system of this invention, for which a very good dimensional stability is vital upon rapid free standing post cure, is to design the matrix resin system such that it can provide a large number of potential reaction sites by using a material with highly functional backbone structures. Another strategy is to use coreactant and/or catalyst molecules which are very small and active so that they can undergo a great deal of molecular motion and can diffuse through a vitrified system very quickly. The catalyst used has to be slightly latent, to yield enough work-life for making big tools, which may last 2–3 days. The ideal system should have about 2–3 days work-life and should be able to finish the initial room temperature cure in seven days, after which the tool will be demolded and processed further, if desired. As discussed in the referenced application in which this system is initially disclosed, different cyanate-imidazole adducts exhibit different solubility parameters in different resin systems. The right type of catalyst and amount should be determined, through routine experimentation, in order to formulate a particularly successful system. While the catalyst should not be quite soluble in the system at cure temperature (20°–25° C.) initially, it is necessary that it dissolve completely into the epoxy resin mixture after 2–3 days. If complete solubility of the selected catalyst is not achieved after the epoxy resin or resin mixture has gelled, the laminates and tool made will exhibit poor properties.

The prepared prepreg system of this invention has an extended freezer shelf-life (temperatures about 0°). No maximum shelf life has yet been determined, but samples properly stored for over 6 months have been demonstrated to be workable and demonstrate undiminished physical properties.

Although the selection of particular resins and catalysts will depend on the ultimate properties desired, one particular high performance system, giving a tool which can be subsequently cured to high temperatures and give excellent performance include high crosslinking density epoxy resins such as MY720 and Araldite MY-0500 manufactured by Ciba, resin SU-8 manufactured by Interez, Inc. and resin 7342, available from Dow Chemical. Typical selections are set forth below.

|  | pph |
| --- | --- |
| Ciba Araldite MY-0500 | 40 |
| Ciba MY720 | 10 |
| Interez, Inc. SU-8 (100% Solid. Same as EpiRez 2390, which comes in acetone, 75% by weight). | 30 |
| Dow XD7342 | 20 |
| Catalyst | 12.5 |

EXAMPLE 1

Manufacturing Tooling Prepregs

1. Dissolve the XD7342 75% in acetone. This can be done in either of two ways:
   a. On a drum roller for 12–24 hours, or
   b. By adding small amounts of broken chunks to stirred acetone with mild (120° F. heating). This will take less time (4–5 hours) depending on the size of the batch. Cool the solution to ambient temperature.

2. EpiRez 2390 (same as SU-8 which is 100% solid) comes with 75% by weight in acetone. Blend the 2390 and the XD7342 solutions with good mixing.

3. 0500 resin from Ciba was added slowly with stirring.

4. Preheat the MY-720 to 140°–180° F. to make it transferable and add to the above solution while stirring. Cool the final solution to ambient temperature.

5. A 32% by weight of the Dicyanate-imidazole catalyst of the invention in acetone is ball-milled to a fineness of at least 8 (north scale; maximum fineness) on a grind gauge. It takes anytime from 4 to 12 hours depending on the size of the batch. The pasty mixture is then transferred to the epoxy solution with good stirring to avoid the settlement of the catalyst to the bottom.

6. The whole mix is stirred at least 15 minutes. This gives the final resin mixture a 72.5% solid in acetone. This solid % should be adequate for a 40% resin pick up on 12K standard graphite fiber 690 weave graphite.

EXAMPLE 2

Physical Properties

The panels for these tests were constructed from the tooling prepregs of Example 1, in the form of a 10×10 box woven layed up to an eight ply quasiisotropic laminate and cured under vacuum bag pressure only. A 1° F./min ramp rate was used when post curing to 200° F. and 3° F./min postcure from 200° F. to 350° F. The thermal cycling test used a 5° F./min ramp rate.

| ALL SAMPLES CURED FOR 7 DAYS AT 77° F. FOLLOWED BY POSTCURE AS INDICATED | | | |
|---|---|---|---|
| | at 77° F. | | |
| | 7 Days | 10 Days | 15 days |
| Flexural strength and Modulus tested at 77° F. with no postcure (KSI/msi) | 40/6.1 | 76/6.2 | 106/6.2 |
| Flexural strength and modulus tested at 77° F. after 4 hours postcure at 200° F. | 90/8.2 | | |
| Flexural strength and modulus tested at 77° F. after 4 hours at 200° F. and 2 hours at 350° F. | 102/8.4 | | |
| Flexural strength and modulus tested at 200° F. after 4 hours at 200° F. | 80/7.9 | | |
| Flexural strength and modulus tested at 350° F. after 200° F. and 350° F. postcure | 30/5.6 | | |
| Flexural strength and modulus tested at 77° F. after all postcures and 33 thermal cycles to 350° F. | 90/8.1 | | |
| Flexural strength and modulus at 350° F. after all postcures and 33 thermal cycles to 350° F. | 32/6.0 | | |
| Neuner Sag between 77° F. and 200° F. (mils) | 71 | | |
| Boeing sag between 200° F. and 360° F. (mils) tested after 200° F. postcure | 5 | | |

Sag Test Procedures Tests on 690 style graphite are run on 8-ply quasiisotropic laminates with 40% resin content.

1. Cut into 11 by 1 inch pieces, 0 or 90 degrees parallel to the 11 inches.

2. Drill hole half of inch (½") from one end and middle with #50 drill, sand lightly by hand to get rid of any burrs caused by the drill.

3. Get a glass plate and mark an area that you will always put this 11 by 1 inch sample on. Measure the maximum thickness which fits under the middle of the specimen with a feeler gauge. Mark "top" on the top of the specimen and an arrow showing the direction to stick in the feeler gauge.

4. "Neuner" Sag - Put specimen in the sag test fixture with hole end out and "top" on top. Hang 12 oz. weight with steel wire and washer. Clamp down the other end of the specimen with a one inch overlap. The specimen was put into the programmed oven so weight hangs free. Set the oven at 1° F./min to 200° F. and then hold for 4 hours at 200° F. The cooling rate was also 1° F./min. Remove the specimen from the fixture at R.T. Measure the middle distance again under specimen where the arrow was. The difference between this number and the original number is sag in mils.

5. Modified Boeing Sag*- Place sample into the programmed oven with same post cure cycle as #4 above but without a weight and supported or lying on a flat surface. The sample was cooled down to ambient temperature at 1° F./min. Measure the middle distance and mark "top" and arrow. The 200° F. postcured sample was placed into the test fixture with the same 12 oz. weight with a ramping temperature of 10° F./min to 400° F., hold 1 hour then cool to ambient temperature again at 10° F. min. The middle distance was again measured. Difference as in #4 above is the modified Boeing sag in mils.

* The word "modified" was used before the Boeing Sag only because Boeing runs this test on a panel that has been curd 8 hours at 200° F.

Many other novolak and multi-functional epoxy resins, such as Dow Chemical's DEN-438 and TACTIX-742, resins available from Shell, Co. under the designations EPON-1071 and EPON-1031, and a variety of other resins, including those available from Interez can be used or otherwise substituted to obtain the particular balance of properties desired. The catalyst level should be above 8 ppm in all mixtures, to obtain a cure period of 7–10 days at room temperature.

In addition to the advantages discussed above, the tooling of this invention has particular advantages in that the resin system used has a long room temperature work-life of 2–3 days or more, such that extremely large, or complicated parts can be prepared. Of course, the freezer storage life of this system is excellent, over 6 months or more. The resulting dimensional stability is excellent, even after a free standing post cure with a very fast cure profile (no particular heating ramp). As the master necessary to prepare the room temperature free standing article is not exposed to high temperatures, very inexpensive low temperature patterns can be employed, with a significant cost savings, yet resulting in a tool which, as discussed above, has an extended useful life. Additionally, the very low exothermic nature of this system is suited to the manufacture of very large structures, in that a preparation of a large mass can be safely undertaken, without fear of high exotherm reaction problems.

Obviously, numerous modifications and variations of the present invention are possible in light of the above teachings. It is therefore to be understood that within the scope of the appended claims, the invention may be practiced otherwise than as specifically described herein.

What is claimed is:

1. A composite tooling prepreg, comprised of an epoxy resin system and reinforcing material, said epoxy resin system comprising a catalyst of the formula

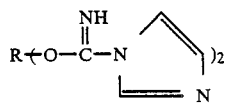

wherein R is aromatic or aralkyl, and wherein the 2, 4 and 5 positions of the imidazole of said formula are independently unsubstituted or substituted with $C_{1-12}$ alkyl, aryl or aralkyl, and an epoxy resin, said tooling prepreg being in a form capable of being cured to form a tooling which can be used for repeated molding of composite parts.

2. The prepreg of claim 1, wherein said catalyst and said resin are selected so as to provide for a work life, at room temperature, of 2–3 days.

3. The prepreg of claim 1, wherein said tool may be cured to a free standing state at room temperature in approximately 7–10 days.

4. The prepreg of claim 1, which, after initial cure such that it is free standing at room temperature, is subjected to a subsequent free-standing post cure at elevated temperatures up to about 370° F.

5. The prepreg of claim 1, wherein said reinforcement is comprised of high modulus fibers.

6. The prepreg of claim 5, wherein said fibers are selected from the group consisting of fiberglass, graphite, boron and mixtures thereof.

7. A method of making a composite tooling part comprising:

preparing a prepreg of a reinforcing material in a matrix of an epoxy resin system comprised of a catalyst of the general formula:

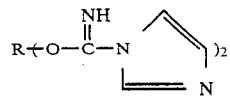

wherein R is aromatic or aralkyl, the 2, 4 and 5 positions of the imidazole ring are independently unsubstituted or substituted with $C_{1-12}$ alkyl, aryl or aralkyl, and an epoxy resin, shaping said prepreg into the desired form of said tool, initially curing said tool in a mold at low temperatures, such that said tool becomes free standing at room temperature.

8. The process of claim 7, which further comprises post-curing said tool at temperatures up to 370° F.

9. The process of claim 7, wherein said catalyst and resin are selected so as to give a work life of 2–3 days.

10. The process of claim 7, wherein said initial cure is performed by allowing said prepreg to remain, in said mold, at room temperature, until it is free standing.

11. The process of claim 10, wherein said room temperature curing lasts for 7–10 days.

12. The process of claim 7, wherein said prepreg is prepared by incorporating in said resin system high modulus reinforcing fibers.

13. The process of claim 12, wherein said fibers are selected from the group consisting of fiberglass, graphite, boron and mixtures thereof.

14. The process of claim 7, wherein said initial curing is accelerated by increasing the exposure temperature up to about 250° F.

15. The process of claim 7, wherein said prepreg is stored up to 6 months in a freezer prior to said shaping and curing stages.

* * * * *